(12) United States Patent
Akamatsu et al.

(10) Patent No.: US 8,310,536 B2
(45) Date of Patent: Nov. 13, 2012

(54) SHAPE MEASUREMENT APPARATUS AND SHAPE MEASUREMENT METHOD

(75) Inventors: Masaru Akamatsu, Kobe (JP); Hidehisa Hashizume, Kobe (JP); Yasuhide Nakai, Kobe (JP)

(73) Assignee: Kobelco Research Institute, Inc., Hyogo (JP)

( * ) Notice: Subject to any disclaimer, the term of this patent is extended or adjusted under 35 U.S.C. 154(b) by 563 days.

(21) Appl. No.: 12/452,230

(22) PCT Filed: Jul. 18, 2008

(86) PCT No.: PCT/JP2008/063062
§ 371 (c)(1),
(2), (4) Date: Dec. 22, 2009

(87) PCT Pub. No.: WO2009/011432
PCT Pub. Date: Jan. 22, 2009

(65) Prior Publication Data
US 2010/0134615 A1    Jun. 3, 2010

(30) Foreign Application Priority Data

Jul. 18, 2007  (JP) .................................. 2007-186896

(51) Int. Cl.
*H04N 7/18* (2006.01)
(52) U.S. Cl. ........ 348/135; 348/125; 348/126; 348/128; 348/133; 348/137
(58) Field of Classification Search .................. 348/125, 348/126, 128, 133, 135, 137
See application file for complete search history.

(56) References Cited

U.S. PATENT DOCUMENTS

| 5,555,091 | A |   | 9/1996 | Kagamida |
|-----------|---|---|--------|----------|
| 6,095,897 | A |   | 8/2000 | Stocker et al. |
| 6,102,777 | A | * | 8/2000 | Duescher et al. ............... 451/36 |

(Continued)

FOREIGN PATENT DOCUMENTS

JP        07-218228         1/1994
(Continued)

OTHER PUBLICATIONS

Office Action (Notification of Reasons for Refusal) from Japanese Patent Office dated Oct. 7, 2008.

(Continued)

*Primary Examiner* — Sath V Perungavoor
*Assistant Examiner* — Geepy Pe
(74) *Attorney, Agent, or Firm* — Stites & Harbison, PLLC; Juan Carlos A. Marquez, Esq

(57) ABSTRACT

An apparatus and method are provided for measuring the end surface of a disk-shaped semiconductor wafer based on its projection image, without the influence of contaminants on the end surface. A rotation supporting mechanism supports a wafer between a first supporting position rotated by $+\delta$ relative to a predetermined reference position and a second supporting position rotated by $-\delta$ degrees at two or more supporting positions. An image sensor picks up a projection image of the wafer's end surface. An index value for the end surface is calculated for each of a plurality of obtained projection images. One representative value of the calculated index values or an aggregate value is obtained, and a shape measurement of the wafer's end surface corresponding to the reference supporting position is derived. When the wafer's radius and a chamfer width are set as r and k, $\delta \geq \cos^{-1}((r-k)/r)$ is satisfied.

20 Claims, 6 Drawing Sheets

U.S. PATENT DOCUMENTS

| | | |
|---|---|---|
| 6,149,506 A * | 11/2000 | Duescher .................... 451/59 |
| 6,217,420 B1 | 4/2001 | Stocker et al. |
| 6,224,459 B1 | 5/2001 | Stocker et al. |
| 6,267,647 B1 | 7/2001 | Stocker et al. |
| 2001/0000502 A1 | 4/2001 | Stocker et al. |
| 2006/0109484 A1 | 5/2006 | Akamatsu |

FOREIGN PATENT DOCUMENTS

| | | |
|---|---|---|
| JP | 06-174445 | 6/1994 |
| JP | 07-218228 | 8/1995 |
| JP | 2001-150159 | 11/1999 |
| JP | 2000-512565 | 9/2000 |
| JP | 2001-004341 | 1/2001 |
| JP | 2001-150159 | 6/2001 |
| JP | 2006-145487 | 11/2004 |
| JP | 2006-145487 | 6/2006 |
| WO | WO 97/48525 | 12/1997 |

OTHER PUBLICATIONS

Notification of Reason(s) for Refusal dispatched by the Japanese Patent Office on Jan. 18, 2011 in Patent Application No. 2008-310183 (2 pages) with an English language translation (2 pages).

Office Action issued by the German Patent and Trade Mark Office on Mar. 28, 2011 in the corresponding Patent Application No. 11 2008 001 894.4-54 (5 pages) with an English language translation (5 pages).

International Search Report mailed Oct. 7, 2008.

* cited by examiner

SHAPE MEASUREMENT APPARATUS AND SHAPE MEASUREMENT METHOD

TECHNICAL FIELD

The present invention relates to a shape measurement apparatus and a shape measurement method for measuring a shape of a chamfer processed surface in an end part (end surface) of a disk-shaped measurement target (such as mainly a semiconductor wafer, and in addition, an aluminum substrate and a glass substrate for a hard disk) on the basis of a projection image thereof.

BACKGROUND ART

At a time of manufacturing a semiconductor wafer (hereinafter, referred to as wafer) or a time of manufacturing a device using the wafer, an end part (edge part) of the wafer may be damaged or chipped by being contacted with another component or a wafer holding member in some cases. Furthermore, the wafer may also be cracked because of the scratch or chip. Probability of this scratch or chip in the end part of the wafer is considered to have a relation with a shape of an end surface of the wafer (so-called edge profile part). For this reason, it is important to correctly measure an edge profile of a disk-shaped measurement target represented by the wafer. It should be noted that the shape of the end surface herein is a profile in a thickness direction (one-dimensional direction) of the wafer, that is, a cross-sectional shape in the thickness direction, which is hereinafter referred to as edge profile.

A representative example of a measurement method for the edge profile is a nondestructive inspection method (SEMI-MF-928-0305 Specification Method B) regulated by Semi Standard which is a standard specification established by an industry organization related to semiconductor manufacturing apparatuses/materials (Semiconductor Equipment and Materials International: hereinafter, referred to as SEMI). This nondestructive inspection method is a method including transmitting light to the chamfer processed end part of the disk-shaped wafer in a direction substantially parallel to the respective front and rear surfaces of the wafer (first direction), picking up a projection image of the wafer by a camera from a direction opposite to the light transmitting direction, and measuring the shape of the end surface of the wafer on the basis of the projection image (hereinafter, referred to as light projection measurement method). A contour of a projection image obtained through this light projection measurement method represents a cross-sectional shape of the end surface of the wafer (a cross-sectional shape cut in the thickness direction).

The light projection measurement method is, for example, illustrated as a shape detection method based on a shape detector for detecting the cross-sectional shape of the wafer in Patent Document 1. Also, in Patent Document 2, in the light projection measurement method, an optical system for preventing generation of contour blurriness or diffraction stripes in a projection image is proposed.

FIG. 3(a) shows an example of the projection image (black shadow part) obtained by picking up an image of an end surface of a wafer 1 through the light projection measurement method.

Also, a main objective of the measurement of the edge profile is to evaluate whether or not the end surface shape falls into an allowable range with respect to a previously set design shape (suitability). For this reason, in the measurement of the edge profile, normally, with respect to the projection image of the wafer end surface, a previously set image processing is executed to calculate index values of the end surface shape and the suitability is determined depending on whether or not the calculated index values fall into allowable ranges. The index values include, for example, a chamfer width k of the end surface of the wafer, a chamfer angle θ, a chamfer radius rm (also referred to as edge R, etc.) and the like.

FIG. 4 is an explanatory diagram for describing an example of the index values of the edge profile of the wafer. As shown in FIG. 4, the chamfer width k is a width from a border position Q1 (or Q2) of the front or rear surface (mutually substantially parallel surfaces) of the wafer and a chamfered part E (end surface) of the end part to a tip of the chamfered part (end surface) (a length in the direction parallel to the front or rear surface (radius direction of the wafer 1)) in the projection image. Also, the chamfer angle θ is an angle defined by an extended line of the front and rear surfaces of the wafer 1 and a tangent line with respect to the surface of the chamfered part E (end surface) in the vicinity of the border position Q1 (or Q2) in the projection image. Also, when the chamfered part E (end surface) is approximated by a circular arc, the chamfer radius rm is a radius of the circular arc.

Patent Document 1: Japanese Unexamined Patent Application Publication No. 7-218228
Patent Document 2: Japanese Unexamined Patent Application Publication No. 2006-145487

DISCLOSURE OF INVENTION

Problems to be Solved by the Invention

Incidentally, as a measurement field for a measurement target which is a precision component such as a wafer (semiconductor wafer) keeps a clean environment in general, dust or the like adheres to the measurement target at a low frequency, but in rare cases, a state occurs in which a contaminant such as the dust exists on the measurement target. Then, in the light projection measurement method, if the contaminant such as the dust at the measurement site (end surface) of the wafer (measurement target), depending on the position of the contaminant, the projection image of the contaminant may appear on the projection image of the wafer end part as a protrusion part. FIG. 3(b) schematically shows a situation in which the projection image of the contaminant appears on the projection image (black shadow part) obtained by picking up an image of the end surface of the wafer 1 through the light projection measurement method. It should be noted that the size of the projection image of the contaminant in FIG. 3(b) does not necessarily represent the size of the actual contaminant in the wafer 1.

As shown in FIG. 3(b), when the image of the contaminant such as the dust appears on the projection image obtained through the light projection measurement method, an issue exists that the end surface shape (index value thereof) of the measurement target cannot be accurately measured, and a wafer that should be judged as a conforming product in a case where the contaminant does not exist is misjudged as a nonconforming product.

Therefore, the present invention has been made in view of the above-mentioned circumstances, and an object thereof is to provide a shape measurement apparatus and a shape measurement method in which in a case where a shape of an end surface of a disk-shaped measurement target such as a semiconductor wafer is measured on the basis of a projection image thereof, it is possible to perform a correct shape measurement without suffering an influence of a contaminant existing on the end surface.

Means for Solving the Problems

In order to achieve the above-mentioned object, a shape measurement apparatus according to the present invention is, for example, an apparatus for transmitting light by light transmission means to a chamfer processed end part of a disk-shaped measurement target such as a semiconductor wafer from a direction substantially parallel to respective front and rear surfaces of the measurement target and also picking up a projection image of an end surface of the measurement target by image pickup means from a direction opposite to the light transmitting direction to measure the shape of the end surface of the measurement target on the basis of the projection image, and further is provided with the following respective components (1-1) to (1-5).

(1-1) A rotation supporting mechanism configured to rotatably support the measurement target in a circumferential direction thereof.

(1-2) Rotation control means configured to support the measurement target by the rotation supporting mechanism in a range from a first supporting position rotated by a predetermined first set angle with respect to a predetermined reference supporting position to a second supporting position rotated by a predetermined second set angle having an opposite positive or negative sign with respect to the first set angle at two or more supporting positions including the first supporting position and the second supporting position.

(1-3) Image pickup control means configured to pick up by the image pickup means the projection image of the end surface of the measurement target supported by the rotation control means at the two or more supporting positions.

(1-4) Index value calculation means configured to calculate an index value of an end surface shape by executing a previously set image processing for each of a plurality of projection images obtained through a processing by the image pickup control means.

(1-5) Measurement value derivation means configured to derivate a measurement value for the shape of the end surface of the measurement target corresponding to the reference supporting position by selecting one representative value based on the plurality of index values calculated by the index value calculation means or calculating one aggregate value while following a previously set rule.

For example, it is conceivable that the rotation control means supports the measurement target by the rotation supporting mechanism at three or more supporting positions including the reference supporting position, the first supporting position, and the second supporting position, and the image pickup control means picks up by the image pickup means the projection image of the end surface of the measurement target supported at each of the three or more supporting positions by the rotation control means.

As the measurement field for the measurement target which is the precision component such as the wafer (semiconductor wafer) keeps the clean environment in general, a state hardly occurs in which a plurality of contaminants adheres at the same time in a relatively narrow area in the measurement target. Then, in the remote chance, even in a case where the contaminants exist at one location of the end part of the measurement target, it is an extremely high possibility that at least one of the plurality of projection images obtained by the image pickup control means has no projection image of the contaminant appearing (not formed as a protrusion part of a contour).

On the other hand, the end surface shape in the measurement target such as the wafer can be generally regarded as the same shape in the relatively narrow area.

Therefore, when the selection of one representative value or the calculation of one aggregate value is performed on the basis of the plurality of index values obtained by the index value calculation means, it is possible to obtain the measurement value with no influence of the contaminant or the extremely small influence of the contaminant for the representative value or aggregate value (the evaluation value for the end surface shape).

The previously set rule for the selection of one representative value is, for example, a rule of selecting a median value, a smallest value, or a largest value among the plurality of the index values and the like. Also, the rule for the calculation of one aggregate value is, for example, a rule of calculating an average value for a previously set numbers of values (including all the values) in an order from a smaller one or a larger one among the plurality of index values and the like.

Also, it is conceivable that the index value is any one of the chamfer width of the end surface of the measurement target, a chamfer angle, and a chamfer radius. The contents of these index values are as already described on the basis of FIG. 4.

Also, in a case where the first set angle is denoted by +δ1 and the second set angle is denoted by −δ2, it is more preferable if δ1 and δ2 satisfy the following (a1) expression:

$$\delta 1 \geq \cos^{-1}((r-k)/r)$$

$$\delta 2 \geq \cos^{-1}((r-k)/r) \tag{a1}$$

r: Radius of the measurement target
k: Chamfer width of the end surface of the measurement target.

It should be noted that δ1 and δ2 may be the same value (δ1=δ2).

As will be described below, in the remote chance, even in a case where the contaminants exist at one location of the end part of the measurement target, if δ1 and δ2 satisfy the following (a1) expression, as will be described below, at least one of the plurality of projection images obtained by the image pickup control means certainly has no projection image of the contaminant appearing (not formed as the projection part of the contour).

For example, in the wafer (disk-shaped), the nonconforming (nonstandard) end surface shape may be generated due to crystal orientation thereof, but an accuracy in a chamfer process is often secured to a degree that the end surface shape at positions of seven locations except for a notch (a part where a recess is formed) or an oriented flat part (a part processed to be flat) among eight locations where the center angle in the end surface (circumferential surface) is shifted by 45 degrees each and the end surface shape in a neighborhood area for each of the seven locations can be regarded as the same shape. Then, in the measurement target such as a semiconductor wafer, and an aluminum substrate and a glass substrate for a hard disk, a ratio (k/r) of the chamfer width k (for example, the chamfer width in design) to the radius r (for example, the radius in design) is small, δ1 and δ2 can be set as relatively small values, and if a difference in the supporting angle of the measurement target is in a range of such a relatively small angle (center angle), the end surface shapes of the measurement target can be regarded as the same shape.

Therefore, with regard to the picked up image under a condition where δ1 and δ2 satisfy the (a1) expression, when the selection of one representative value or the calculation of one aggregate value is performed on the basis of the plurality of index values obtained by the index value calculation means, it is possible to obtain the measurement value with no influence of the contaminant or the extremely small influence of the contaminant for the representative value or aggregate value (the evaluation value for the end surface shape).

Also, in order to avoid that a difference between a front surface shape at the measurement site (end surface) of the measurement target supported at the reference supporting position and a front surface shape in a neighboring part thereof becomes a measurement error, it is desirable that δ1 and δ2 are small in a range satisfying the (a1) expression.

Also, as described above, in a case where the disk-shaped measurement target is the wafer, the accuracy in the chamfer process is often secured to a degree that the end surface shape (cross-sectional shape) at seven locations among eight locations where the center angle in the end surface (circumferential surface) is shifted by 45 degrees each (normally, seven locations except for the notch or the oriented flat part) and the end surface shape in a neighboring range of each of the seven locations (a range of ±22.5 degrees at the center angle) can be regarded as the same shape.

In view of the above, in a case where the disk-shaped measurement target is the wafer, it is preferable that δ1 and δ2 in a case where the first set angle is denoted by +δ1 and the second set angle is denoted by −δ2 satisfy the following (a2) expression:

$$22.5 \geq \delta 1 \geq \cos^{-1}((r-k)/r)$$

$$22.5 \geq \delta 2 \geq \cos^{-1}((r-k)/r) \quad (a2)$$

r: Radius of the semiconductor wafer
k: Chamfer width of the end surface of the semiconductor wafer
where, k/r<0.076.

Incidentally, the semiconductor wafer often has the radius r of about 150 [mm] and the chamfer width k of about 0.35 [mm], but in an intermediate state of the process, the process is performed so as to set the chamfer width k as about 0.10 [mm] at minimum, and a shape measurement for the end surface of the semiconductor wafer subjected to such a process is performed in some cases. As an actual condition of the semiconductor wafer is applied to the (a2) expression that r is about 150 [mm] and k is about 0.10 [mm] or larger as described above, with regard to the semiconductor wafer, it is practical that δ1 and δ2 are respectively in a range between 2° or larger and 22.5° or smaller.

Also, the present invention can also be grasped as a shape measurement method of executing a measurement using the above-illustrated shape measurement apparatus according to the present invention.

That is, the shape measurement method according to the present invention is a shape measurement method including transmitting light by light transmission means to a chamfer processed end part of a disk-shaped measurement target from a direction substantially parallel to respective front and rear surfaces of the measurement target and also picking up a projection image of an end surface of the measurement target by image pickup means from a direction opposite to the light transmitting direction to measure a shape of an end surface of the measurement target on the basis of the projection image and executing the following respective steps illustrated in (2-1) to (2-3).

(2-1) A rotation and image pickup step of supporting the measurement target by a rotation supporting mechanism rotatably supporting the measurement target in a circumferential direction thereof in a range from a first supporting position rotated by a predetermined first set angle with respect to a predetermined reference supporting position to a second supporting position rotated by a predetermined second set angle having an opposite positive or negative sign with respect to the first set angle at two or more supporting positions including the first supporting position and the second supporting position, picking up by the image pickup means a projection image of the end surface of the measurement target supported at the respective supporting positions, and recording image pickup data in predetermined storage means.

(2-2) An index value calculation step of calculating an index value of the end surface shape by executing a previously set image processing by predetermined computation means for each of the plurality of projection images.

(2-3) A measurement value derivation step of executing a processing of deriving a measurement value for the shape of the end surface of the measurement target corresponding to the reference supporting position by predetermined computation means by selecting one representative value based on the plurality of index values calculated in the index value calculation step or calculating one aggregate value while following a previously set rule.

Also, in the shape measurement method according to the present invention, it is conceivable that the previously set rule is any one of a rule of selecting a median value, a smallest value, or a largest value among the plurality of the index values and a rule of calculating an average value for a previously set numbers of values in an order from a smaller one or a larger one among the plurality of index values.

Also, in the shape measurement method according to the present invention too, in a case where the first set angle is denoted by +δ1 and the second set angle is denoted by −δ2, it is conceivable that δ1 and δ2 satisfy the (a1) expression.

Also, in the rotation and image pickup step, it is conceivable that the measurement target is supported by the rotation supporting mechanism at three or more supporting positions including the reference supporting position, the first supporting position, and the second supporting position, and the projection image of the end surface of the measurement target supported at each of the three or more supporting positions is picked up by the image pickup means.

Also, in the shape measurement method according to the present invention, in a case where the measurement target is the semiconductor wafer, it is conceivable that the δ1 and the δ2 satisfy the (a2) expression. For example, it is preferable if the δ1 and the δ2 are respectively in a range between 2° or larger and 22.5° or smaller.

Also, in the shape measurement method according to the present invention, it is conceivable that the index value is any one of the chamfer width of the measurement target, a chamfer angle, and a chamfer radius.

The above-illustrated shape measurement method according to the present invention too exerts a similar action and effect to the shape measurement apparatus according to the present invention described above.

Effects of the Invention

According to the present invention, in a case where the shape of the end surface of the disk-shaped measurement target such as a semiconductor wafer is measured on the basis of the projection image thereof, it is possible to perform the correct shape measurement without suffering the influence of the contaminant existing on the end surface.

REFERENCE NUMERALS

Figure 1:
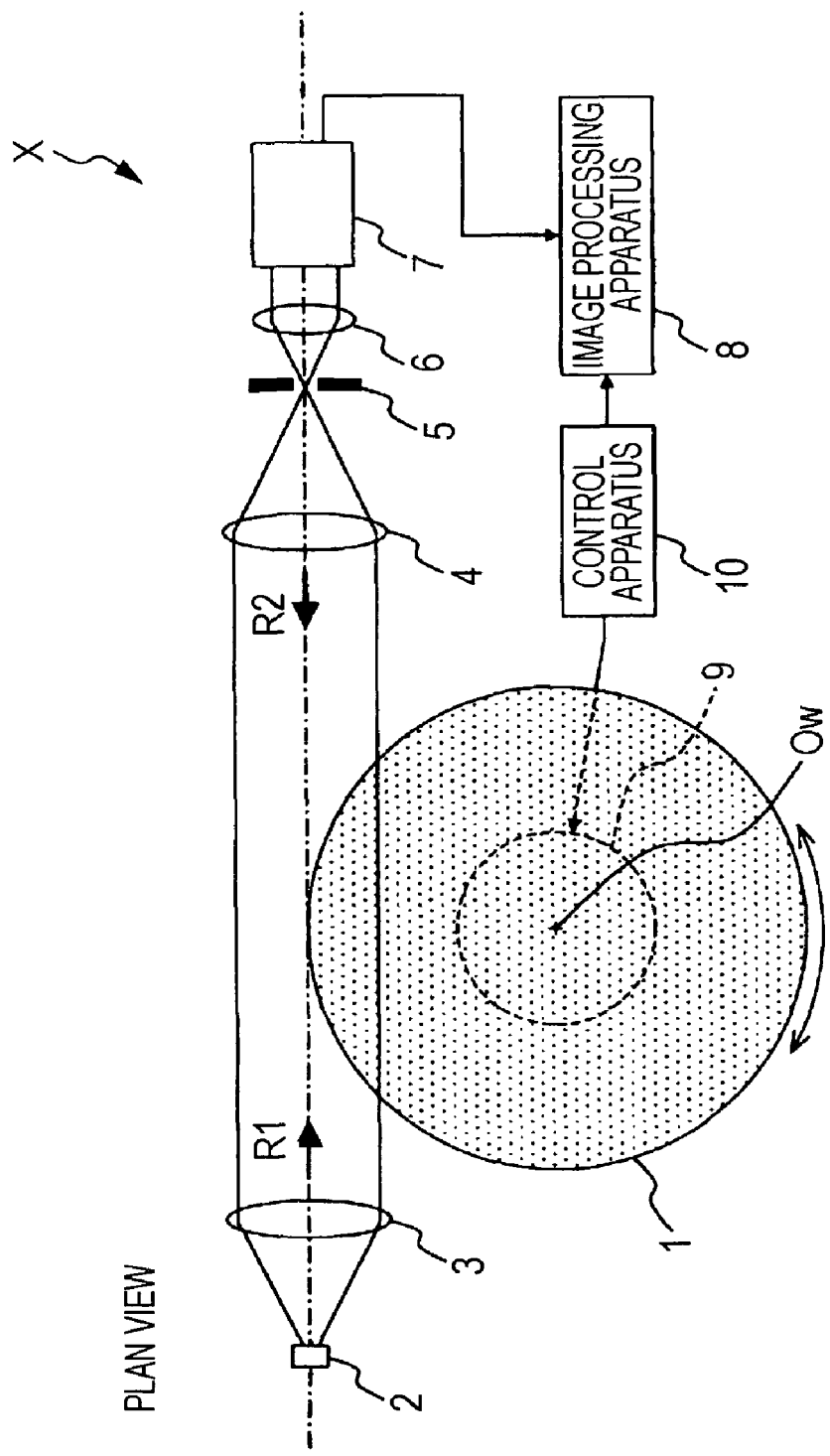
FIG. 1 is a schematic plan view of a shape measurement apparatus X according to an embodiment of the present invention.

X shape measurement apparatus
1 wafer
2 point light source
3 collimator lens
4 first lens
5 aperture
6 second lens
7 image sensor
8 image processing apparatus
9 rotation supporting mechanism
10 control apparatus Best Modes for Carrying out the Invention Hereinafter, with reference to the accompanying drawings, embodiments of the present invention will be described while being devoted for understanding of the present invention. It should be noted that the following embodiments are examples which are crystallization of the present invention and do not have an attribute for limiting the technical scope of the present invention.

A shape measurement apparatus X according to the present invention is an apparatus for transmitting light to a chamfer processed end part of a wafer 1 (semiconductor wafer) which is a disk-shaped measurement target by a light transmission unit from a direction parallel to the respective front and rear surfaces of the wafer 1 and picking up a projection image of the end surface of the wafer 1 by a camera from a direction opposite to the light transmitting direction to measure a shape and a thickness of the end surface of the wafer 1 on the basis of the projection image.

The wafer 1 is composed, for example, of a semiconductor having a radius of about 150 [mm] and a thickness of 0.8 [mm], and an outer peripheral end (peripheral surface) part thereof is chamfer processed.

Hereinafter, with reference to the plan view illustrated in FIG. 1 and the side view illustrated in FIG. 2, a configuration of the shape measurement apparatus X will be described. It should be noted that in FIG. 2, a part of the component shown in FIG. 1 is omitted.

Figure 2:
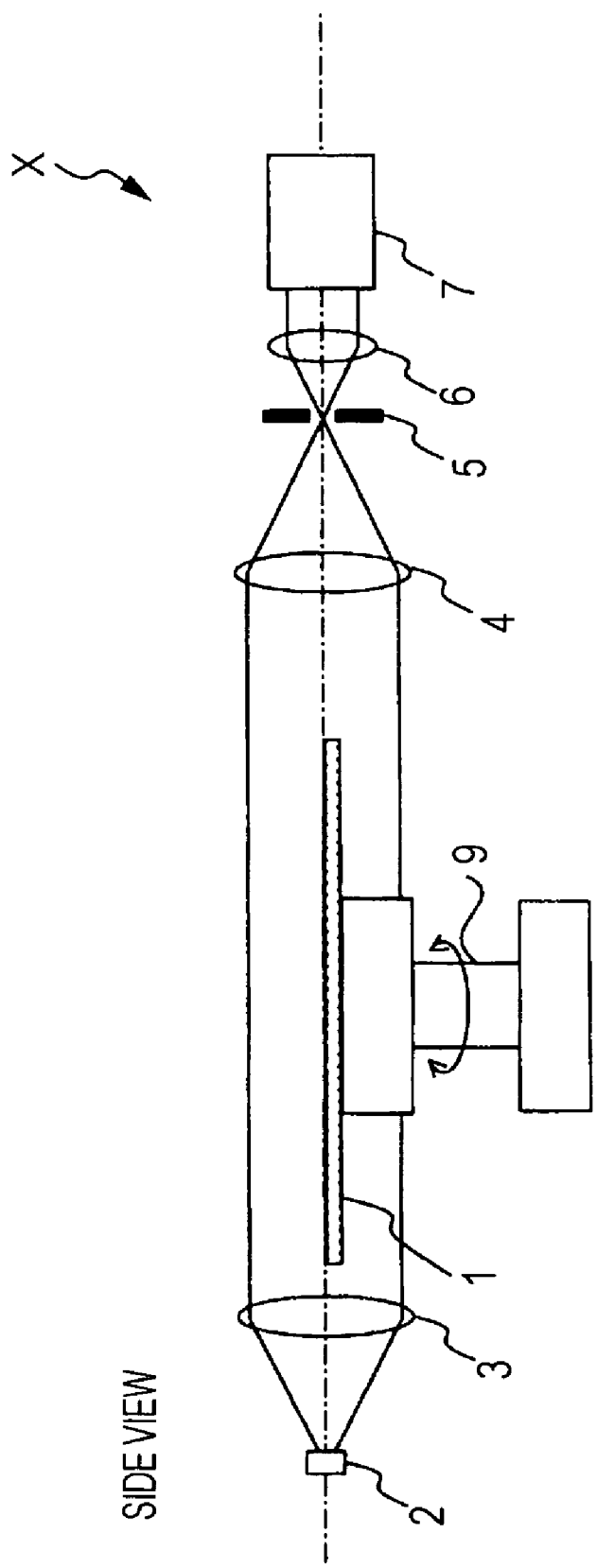
FIG. 2 is a side plan view of the shape measurement apparatus X.
Figure 3:
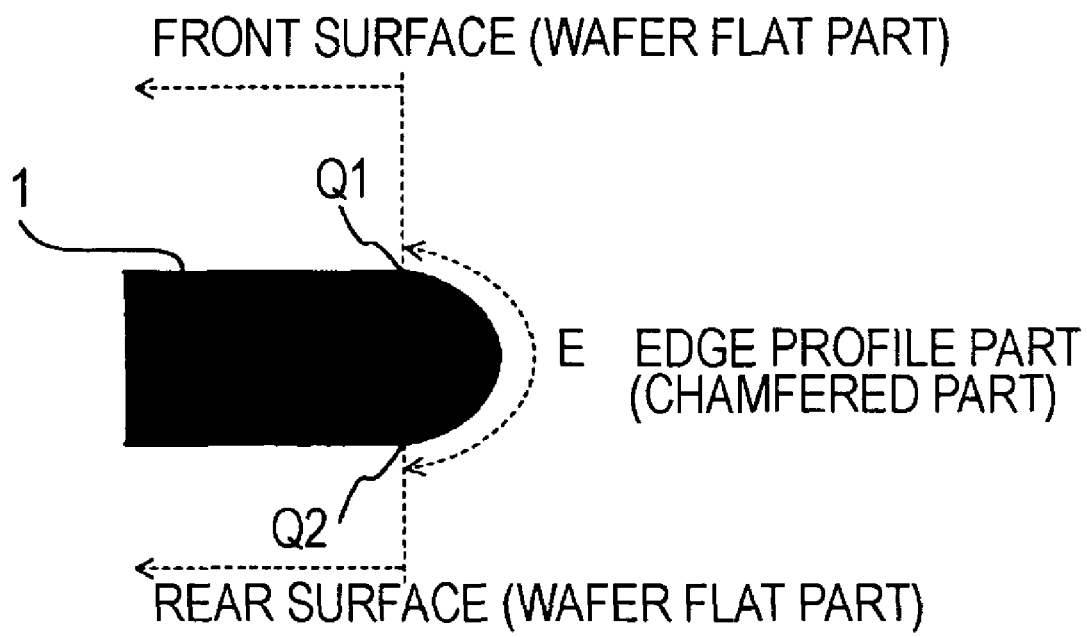
FIG. 3(a) shows an example of a projection image of an end surface of a semiconductor wafer.
FIG. 3(b) shows an example of the projection image of the end surface of the semiconductor wafer.
Figure 3:
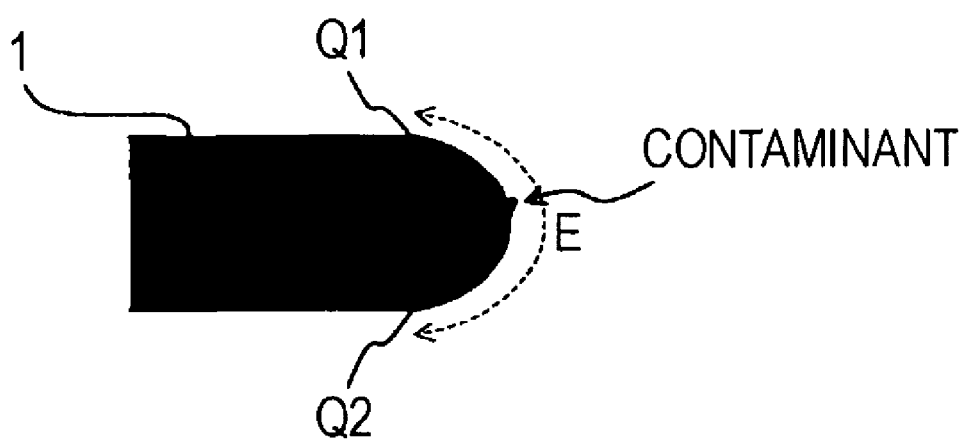

As shown in FIGS. 1 and 2, the shape measurement apparatus X is provided with a point light source 2 as a light transmission unit which is an optical system for the light transmission (an example of light transmission means), and a collimator lens 3 for converting the light of the point light source 2 into parallel light. The parallel light is transmitted to an edge part including the end part of the wafer 1 from a direction R1 parallel to the respective front and rear surfaces of the wafer 1. The point light source 2 is a light source or the like for emitting, for example, light of a white LED through a pin hole having a diameter of 100 μm to 200 μm. A light emission part for the light of the point light source 2 (pin hole) is arranged at a focal position of the collimator lens 3.

Furthermore, the shape measurement apparatus X is provided with a first lens 4, an aperture 5, a second lens 6, and image sensor 7 (such as a CCD) as a camera (equivalent to image pickup means) for picking up a projection image of the edge part including the end part of the wafer 1 from a direction R2 opposite to the light transmitting direction R1 to the wafer 1.

The first lens 4, the aperture 5, and the second lens 6 constitute a telecentric lens, and the light passing there is input to the image sensor 7, so that the projection image of the edge part of the wafer 1 is picked up by the image sensor 7.

An interval (distance) between the collimator lens 3 and the first lens 4 is set, for example, as about 200 [mm], and the edge part of the wafer 1 is arranged in a light path of the parallel light between those.

In this manner, as the shape measurement apparatus X transmits the parallel light to the wafer 1, even when the wafer 1 has a long depth length in a light axis of the parallel light (the light transmitting direction R1), in the image sensor 7, it is possible to obtain the satisfactory projection image in which the degree of blur in the contour is small. Also, by adopting the point light source 2 using the white LED having multi-wavelength components instead of short wavelength light having strong coherency, even when the wafer 1 has the long depth length in the light transmitting direction R1, it is possible to obtain the satisfactory picked up image with fewer diffraction fringes generated in the vicinity of the contour of the projection image in the image sensor 7.

The shape measurement apparatus X is further provided with an image processing apparatus 8, a rotation supporting mechanism 9, and a control apparatus 10.

The image processing apparatus 8 is a computation apparatus for executing an image processing based on the pickup images by the image sensor 7 (images including the projection image of the wafer 1), for example, a DSP (Digital Signal Processor), a personal computer, or the like for executing a predetermined program which is previously stored in a storage unit thereof. As will be described below, the image processing apparatus 8 execute a previously set image processing on the pickup images by the image sensor 7 (projection image) to calculate the index values of the end surface shape of the wafer 1. It should be noted that the image processing apparatus 8 execute an input of the pickup images by the image sensor 7 (image data) and the image processing based on the pickup up images while following a control instruction from the control apparatus 10.

Also, the rotation supporting mechanism 9 is an apparatus for supporting the disk-shaped wafer 1 and also rotating and driving, and stopping the wafer 1 in a peripheral direction thereof while using a center point $O_w$ thereof as a rotation axis to adjust a supporting angle of the wafer 1. The rotation supporting mechanism 9 is provided with a rotation encoder which is not shown and functions as an angle detection sensor for detecting a supporting angle (rotation angle) of the wafer 1 and performs positioning of the supporting position (supporting angle) for the wafer 1 on the basis of the detection angle. It should be noted that the rotation supporting mechanism 9 performs positioning of the supporting position for the wafer 1 while following a control instruction from the control apparatus 10.

The control apparatus 10 is a computer provided with a CPU and peripheral apparatuses thereof and is an apparatus for controlling the image processing apparatus 8 and the rotation supporting mechanism 9 (outputting control instructions) as the CPU executes a control program which is previously stored in a storage unit.

Figure 5:
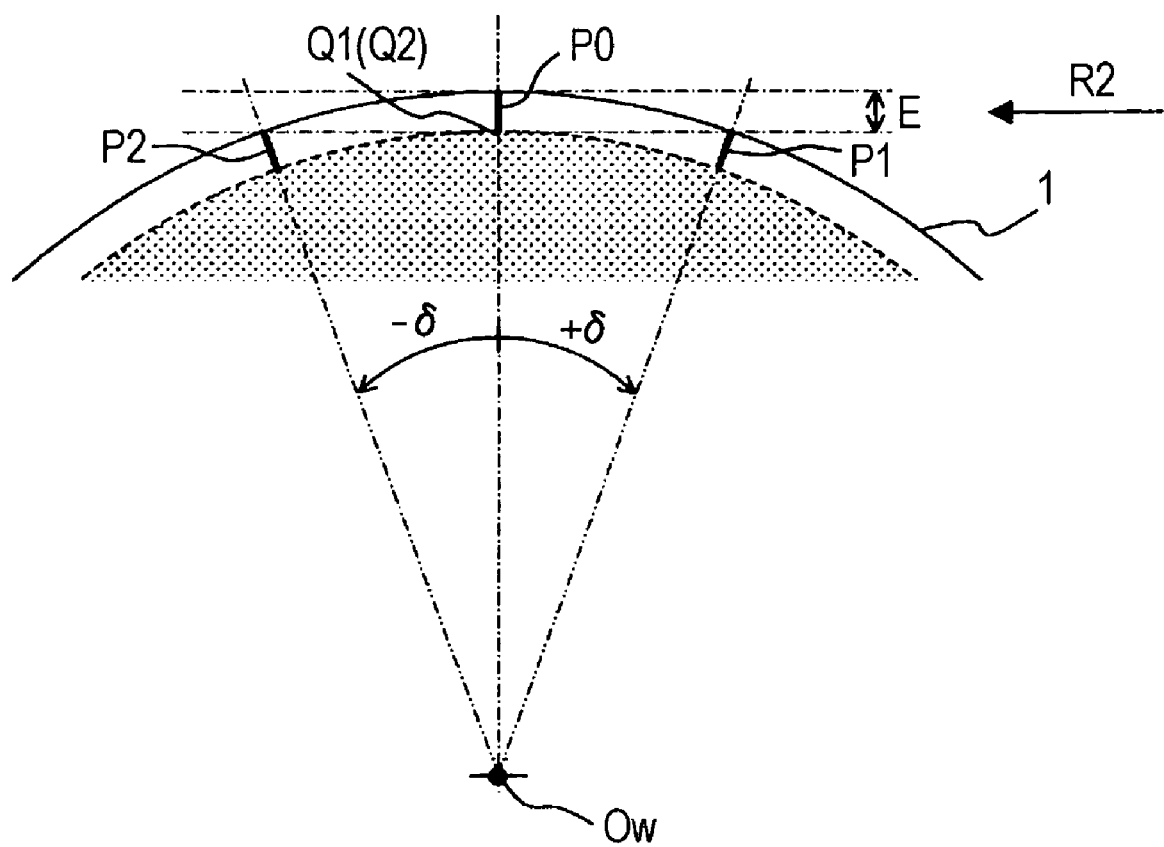
FIG. 5 shows a relation between a supporting angle in the semiconductor wafer and a position of the end part in the semiconductor wafer.

Next, while referring to FIG. 5, a feature of the shape measurement method according to the present invention will be described. FIG. 5 shows a relation between the supporting angle and the position of the end part in the wafer 1.

In FIG. 5, the part (position) indicated by P0 is a position where a contour of a chamfered part of the wafer 1 located at the position becomes the projection image obtained by the shape measurement apparatus X. Herein, the supporting position for the wafer 1 when a site (chamfered part) which becomes an edge profile measurement target for the wafer 1 is located at the position P0 is referred to as reference supporting position.

Now, a case is considered where the wafer 1 is rotated by a predetermined angle ±δ from a state of being supported at this reference supporting position. As shown in FIG. 5, in a case where the wafer 1 is rotated from the reference supporting position by ±δ [degree], a condition for a measurement target site (chamfered part) at a position P0 to move to positions P1 and P2 completely departed from an area E where appearing as the chamfered part (edge profile part) in the projection image is that the angle δ satisfies the following (b1) expression (which is equivalent to the above-mentioned (a1) expression):

$$\delta \geq \cos^{-1}((r-k)/r) \quad (b1)$$

r: Radius of the semiconductor wafer
k: Chamfer width of the end surface of the semiconductor wafer.

For example, in a case where the radius r of the wafer 1 (for example, the radius in design) is 150 [mm] and the chamfer width k of the wafer 1 (for example, the chamfer width in design) is 0.35 [mm], it suffices that δ is 3.9 or larger [degree]. That is, even in a case where one contaminant exists in a predetermined range (relatively close range) including the chamfered part of the wafer 1 in the measurement target site (the site located at the position P0 in the reference supporting position), if the projection images are obtained for the wafer 1 supported at two respective supporting positions including a supporting position rotated from the reference supporting position by +δ [degree] (which is referred to as first supporting position) and a supporting position rotated from the reference supporting position by −δ [degree] (which is referred to as second supporting position), at least one of the two obtained projection images has no influence of the contaminant (the projection image of the contaminant is not formed as the projection part of the contour).

Also, if the projection images are obtained for the wafer 1 supported at three respective supporting positions including the reference supporting position and the respective supporting positions rotated from the reference supporting position by ±δ [degree] (the first supporting position and the second supporting position), at least two of the three obtained projection images have no influence of the contaminant.

On the other hand, the end surface shapes of the wafer 1 can be generally regarded as the same shape in the relatively narrow area, that is, in the wafer 1, the nonconforming (non-standard) end surface shape may be generated due to crystal orientation thereof, but the accuracy in the chamfer process is often secured to a degree that the end surface shape at positions of the remaining seven locations except for the position where a special process is applied such as the notch among eight locations where the center angle in the end surface (circumferential surface) is shifted by 45 degrees each and the end surface shape in a neighborhood area (a range of ±22.5 degrees at the center angle) for each of the seven locations can be regarded as the same shape. Also, in order to conform to M1-1103 of SEMI standard which is a known standard for defining an edge shape of the semiconductor wafer, it is necessary to set the chamfer width of the wafer 1 as about 0.5 [mm], and even when fluctuations of various design conditions are taken into account while this is set as the reference, the chamfer width of the wafer 1 is its two-fold, about 1.0 [mm] about all. Furthermore, as the radius r of the wafer 1 is about 150 [mm], a ratio of the chamfer width k to the radius r of the wafer 1 (k/r) is about 0.0067 (=1.0/150) about all even in the large case, and therefore the angle δ can be set as about 6.6 [degree] at most. If a difference of the supporting angles for the wafer 1 is in a range of such a relatively small angle (center angle) (the reference supporting position ±δ), the end surface shapes of the wafer 1 can be regarded as the same shape.

Therefore, in the measurement using the shape measurement apparatus X for the wafer 1, in the range from the first supporting position up to the second supporting position, the projection image is picked up in the respective states in which the wafer 1 is supported at the two or more supporting positions including the first supporting position and the second supporting position, the index value of the end surface based on each of the plurality of obtained projection images is calculated, and selection of one representative value or calculation of one aggregate value is performed on the basis of the plurality of calculated index values. The thus obtained representative value or aggregate value is a measured value for the shape of the end surface (chamfered part) located at the position P0 when the wafer 1 is supported at the reference supporting position or a shape regarded as the same shape as the above (evaluation value for the end surface shape) and is also a measured value having no influence of the contaminant or extremely small influence of the contaminant.

Figure 4:
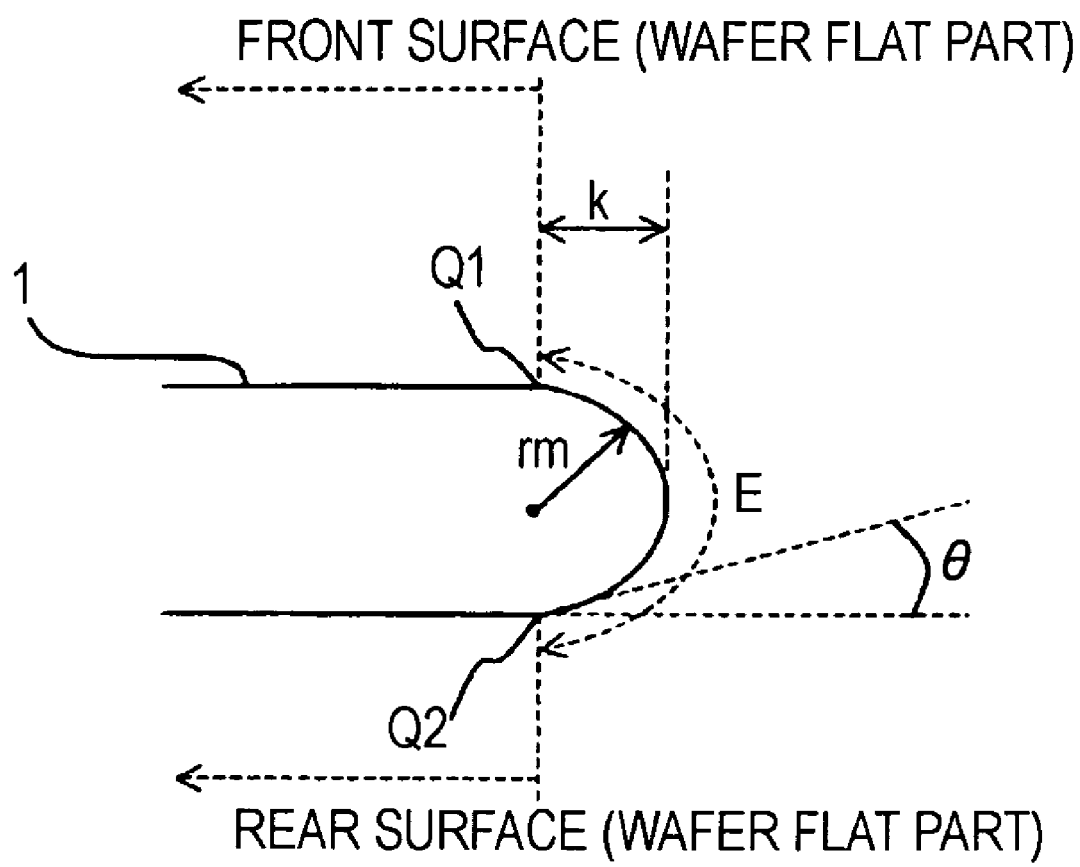
FIG. 4 is an explanatory diagram for describing an example of index values of the edge profile of the semiconductor wafer.

Herein, as the index values, the chamfer width k, the chamfer radius rm, the chamfer angle θ, and the like of the end surface of the wafer 1, and the like are conceivable. The contents of these respective index values are as already described on the basis of FIG. 4.

Also, as a selection method for one representative value, for example, it is conceivable to select a median value, a smallest value, or a largest value from the plurality of index values. The contaminant affects the contour with respect to the projection image in a direction protruding from the end surface shape in a case where the contaminant does not exist. Then, in a case where the contaminant exists in the vicinity of the tip of the end surface of the wafer 1, in general, such a tendency exists that the chamfer width k is calculated larger compared with a case where the contaminant does not exist, and the chamfer radius rm is calculated smaller compared with a case where the contaminant does not exist. On the other hand, in a case where the contaminant exists in the vicinity of the border position between the end surface of the wafer 1 and the respective front and rear surfaces, such a tendency exists that the chamfer width k is calculated smaller compared with a case where the contaminant does not exist, and the chamfer radius rm is calculated larger compared with a case where the contaminant does not exist. For this reason, under a situation in which the position to which the contaminant can be attached is identifiable to some extent, in accordance with types of the index values (the chamfer width k, the chamfer radius rm, the chamfer angle θ, and the like), it is conceivable that the representative value is set as the smallest value and the representative value is set as the largest value. Even in a case where the contaminant exists in the vicinity of the tip of the end surface of the wafer 1, or even in a case where the contaminant exists in the vicinity of the border position between the end surface of the wafer 1 and the respective front and rear surfaces, The chamfer angle θ may be larger or smaller compared with a case where the contaminant does not exits, and therefore it is conceivable to set the representative value as the median value. Also, in a case where three or more index values are calculated, irrespective of the type of the index values, it is conceivable to set the representative value as the median value.

Also, in a case where three or more index values are calculated, it is also conceivable that an average value (an example of the aggregate value) for a previously set numbers of values in an order from a smaller one or a larger one among those index values is calculated, and the average value is set as the measured value.

For example, in a case where three index values are calculated and the index values are the chamfer width k, it is conceivable to set an average value for the two values in an order from the smaller one among the three index values as the measured value. Similarly, in a case where three index values are calculated and the index values are the chamfer radius rm, it is conceivable to set an average value for the two values in an order from the larger one among the three index values as the measured value. It should be noted that it is also conceivable to calculate an average value for all the plurality of calculated index values as the measured value.

Figure 6:
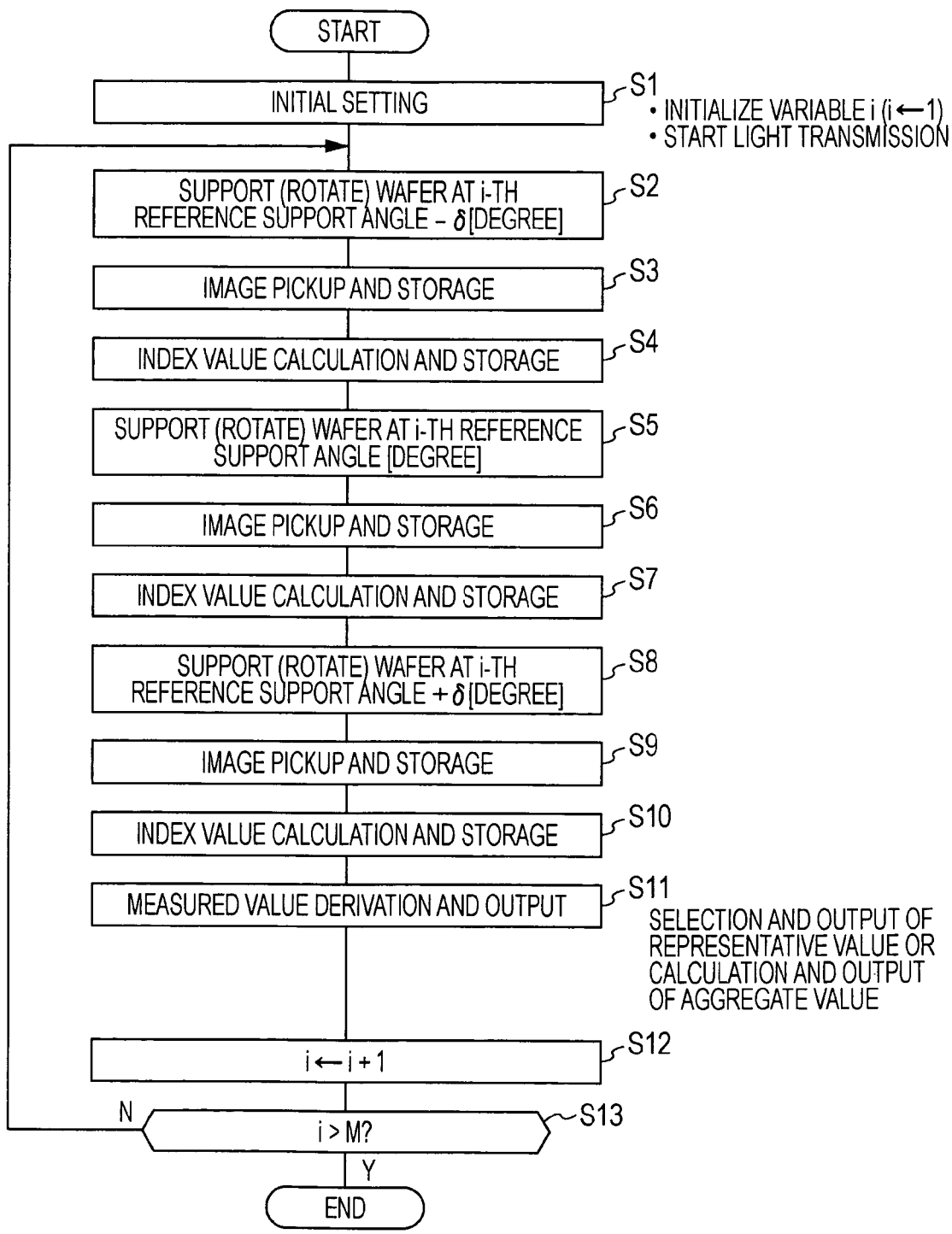
FIG. 6 is a flow chart showing a procedure of a shape measurement processing by the shape measurement apparatus X.

Next, while referring to a flow chart shown in FIG. 6, a procedure for a shape measurement processing (shape measurement method) using the shape measurement apparatus X will be described. It should be noted that S1, S2, . . . illustrated below represent identification symbols for processing procedures (steps).

First, the control apparatus 10 executes an initial setting processing such as an initialization of a predetermined counter variable i (i=1) (S1). At this time, the point light source 2 is turned ON, and light transmission to the wafer 1 is started.

Next, as the control apparatus 10 control the rotation supporting mechanism 9, the supporting position for the wafer 1 (rotation angle) is set so that the wafer 1 is supported at a position rotated by −δ [degree] with respect to the supporting position (the i-th reference supporting position) where the supporting angle (rotation angle of the rotation supporting mechanism 9) is set as a previously set i-th reference supporting angle ψ(i) (S2).

Herein, the reference supporting positions are seven positions (the first to seventh reference supporting positions) among eight positions where the supporting angle for the wafer 1 (rotation angle) by the rotation supporting mechanism 9 is shifted by 45 degrees each except for a case where the notch or the like is at the measurement position.

Also, δ is a setting value representing an angle (previously set setting value) and a setting value satisfying the following (b2) expression (equivalent to the (a2) expression):

$$22.5 > \delta \geq \cos^{-1}((r-k)/r) \quad (b2)$$

r: Radius of the semiconductor wafer
k: Chamfer width of the end surface of the semiconductor wafer
where, k/r<0.076.

A threshold "22.5 degrees" on an upper limit side in this (b2) expression is an angle functioning as a border with the adjacent reference supporting position shifted by 45 degrees. By satisfying this upper limit, in the measurement related to the respective reference supporting positions, the measurement on the measurement site overlapped with the measurement site related to another reference supporting position (chamfered part) can be avoided.

Also, in a case where the radius r of the wafer 1 (for example, the radius in design) is 150 [mm] and the chamfer width k of the wafer 1 (for example, the chamfer width in design) is 0.35 [mm], δ is previously set as 3.9 or larger.

It should be noted that in order to avoid that a difference between the surface shape of the measurement site (end surface) for the wafer 1 supported at the reference supporting position and the surface shape in a neighborhood part thereof becomes a measurement error, the setting value δ representing the angle is desirably even smaller.

In view of the above, it is conceivable that the setting value δ satisfies the following (b3) expression:

$$\delta \approx \cos^{-1}((r-k)/r) \quad (b3)$$

r: Radius of the semiconductor wafer
k: Chamfer width of the end surface of the semiconductor wafer.

For example, in a case where the radius r of the wafer 1 (for example, the radius in design) is 150 [mm] and the chamfer width k of the wafer 1 (for example, the chamfer width in design) is 0.35 [mm], δ is previously set as 4.0 (≈3.9).

Also, as described above, an actual condition for the wafer 1 that the radius r is about 150 [mm] and the chamfer width k is about 0.10 [mm] or larger is applied to the (b2) expression, it is practical that regarding the wafer 1, δ1 and δ2 are respectively in a range from 2° or larger and 22.5° or smaller.

Subsequently, in a state in which the wafer 1 is supported at the position at the i-th reference supporting angle ψ(i)−δ [degree], the projection image of the end surface of the wafer 1 is picked up by the image sensor 7, and furthermore, the control apparatus 10 controls the image processing apparatus 8, so that the picked up image (image data) is taken in to be stored in a predetermined storage unit (a memory or the like provided to the image processing apparatus 8) (S3).

Furthermore, while following a control instruction of the control apparatus 10, the image processing apparatus 8 (an example of the predetermined computation means) executes a previously set image processing on the basis of the picked up image (the image of the projection image of the wafer 1 end part) taken in step S3, calculates the index value of the end surface shape of the wafer 1, and stores the calculated value in the predetermined storage unit (the memory or the like provided to the control apparatus 10) (S4).

For example, in this step S4, the image processing apparatus 8 calculates the chamfer width k of the end surface of the wafer 1 (chamfered part) as the index value.

It should be noted that a method of calculating the chamfer width k on the basis of the projection image of the wafer 1 is known in the technical field of the shape measurement for the wafer 1, and a description will be omitted herein.

Next, as the control apparatus 10 controls the rotation supporting mechanism 9, the supporting position for the wafer 1 (rotation angle) is set so that the wafer 1 is supported at the supporting position (the i-th reference supporting position) where the supporting angle (rotation angle of the rotation supporting mechanism 9) becomes a previously set i-th reference supporting angle ψ(i) (S5). That is, from the state in steps S3 and S4, the wafer 1 is rotated by +δ [degree].

Subsequently, in a state in which the wafer 1 is supported at the i-th reference supporting angle ψ(i), the control apparatus 10 and the image processing apparatus 8 execute the same processing as steps S3 and S4 described above (S6, S7).

According to this, the index value (herein, the chamfer width k of the end surface of the wafer 1 (chamfered part)) based on the projection image obtained in a state in which the wafer 1 is supported at the i-th reference supporting angle ψ(i) is calculated and stored.

Furthermore, as the control apparatus 10 controls the rotation supporting mechanism 9, the supporting position for the wafer 1 (rotation angle) is set so that the wafer 1 is supported at the supporting position where the supporting angle (rotation angle of the rotation supporting mechanism 9) is at a previously set i-th reference supporting angle ψ(i)+δ [degree] (S8). That is, the wafer 1 is rotated from the state in steps S6 and S7 by +δ [degree].

Subsequently, in a state in which the wafer 1 is supported at the angle of the i-th reference supporting angle ψ(i)+δ [degree], the control apparatus 10 and the image processing apparatus 8 execute the same processing as steps S3 and S4 described above (S9, S10).

According to this, the index value (herein, the chamfer width k of the end surface of the wafer 1 (chamfered part)) based on the projection image obtained in a state in which the wafer 1 is supported at the angle of the i-th reference supporting angle ψ(i)+δ [degree] is calculated and stored.

The process in steps S2, S3, S5, S6, S8, and S9 described above is a process for supporting by the rotation supporting mechanism 9 the wafer 1 in a range from the supporting position rotated by +δ degrees (hereinafter, referred to as first supporting position) with respect to the i-th reference supporting position to the supporting position rotated by −δ degrees (hereinafter, referred to as second supporting position) at the three supporting positions including the first supporting position, the second supporting position, and the i-th reference supporting position, picking up by the image sensor 7 (an example of the image pickup means) the projection image of the end surface of the wafer 1 supported at the respective supporting positions, and recording the image pickup data in the predetermined storage means and is an example of the rotation and image pickup step. It should be noted that the control apparatus 10 is an example of the rotation control means and the image pickup control means.

Also, the process in steps S4, S7, and S10 described above is a process for executing a previously set image processing for each of the plurality of projection images obtained in the rotation and image pickup process by a processor (computation means) provided to the image processing apparatus 8 to calculate the index value of the end surface shape of the wafer 1 and is an example of the index value calculation process.

Next, the control apparatus 10 executes the selection of one representative value or the calculation of one aggregate value on the basis of the plurality of index values (herein, the chamfer widths k) obtained in the process in steps S2 to S10 while following a previously set rule to derive (select or calculate) the representative value or the aggregation value as the measured value of the end surface shape of the wafer 1 corresponding to the i-th reference supporting position and outputs the measured value through predetermined output means (S11, examples of the measurement value derivation process and the same means). For example, as described above, the control apparatus 10 executes the processing of selecting the smallest value or the median value among the three chamfer widths k (index values) and outputting it as the measured value or the processing of calculating the average value for the two values in the order from the small one among the three chamfer widths k (index values) (an example of the aggregation value) and outputting it as the measured value. It should be noted that as the outputting of the measured value, variations are conceivable such as display of the measured value to a display apparatus, sending of the measured value to another apparatus via communication means, write of the measured value to the storage means.

Next, the control apparatus 10 counts up the counter variable i (+1) (S12) and judges whether or not the counter variable i exceeds the previously set setting value M (S13). Then, when the control apparatus 10 judges that (i>M) is not established, the processing is returns to the above-mentioned step S2, and the processing in steps S2 to S13 is repeatedly performed, and when it is judged that (i>M) is established, the processing is ended.

For example, in the measurement for the wafer 1, M is 7, the first to seventh reference supporting angles ψ(1) to ψ(7) are angles set while being shifted by 45 degrees each (for example, 0 degree, 45 degrees, 90 degrees, 135 degrees, . . . , 270 degrees, and 315 degrees).

According to this, in the shape measurement using the shape measurement apparatus X for the wafer 1, the setting values δ representing the angle (equivalent to δ1 and δ2) satisfy the (b2) expression (that is, the (b1) expression is also satisfied), and for each of the seven reference supporting positions (i=1 to 7) among the eight supporting positions where the supporting angle for the wafer 1 is shifted by the rotation supporting mechanism 9 by 45 degrees each, the respective processes in steps S2 to SS11 (equivalent to the rotation and image pickup process, the index value calculation process, and the measurement value derivation process) are executed. It should be noted that depending on a measurement requirement, the respective processes in steps S2 to SS11 may be executed in some cases for only six or five reference supporting positions (supporting positions in plural patterns other than the seven patterns) among the eight supporting positions where the supporting angle for the wafer 1 is shifted by 45 degrees each. Also, the respective processes in steps S2 to SS11 while a plurality of supporting positions where the supporting angle for the wafer 1 is shifted by an angle each other than 45 degrees (for example, 15 degrees) are set as the reference supporting positions.

Through the above-illustrated shape measurement using the shape measurement apparatus X for the wafer 1, when the shape of the disk-shaped end surface of the wafer 1 is measured on the basis of the projection image, it is possible to perform the correct shape measurement without receiving the influence of the contaminant existing on the end surface.

Also, the action and effect illustrated above can be obtained similarly even in a case where the same of the surface at a chamfer processed end part (end surface) of another disk-shaped measurement target (the aluminum substrate and the glass substrate for the hard disk, and the like) other than the wafer 1 is measured on the basis of the projection image.

Also, the respective absolute values (δ) of +δ and −δ which are the rotation angles with respect to the reference supporting position according to the above-mentioned embodiment do not need to be necessarily the same values, and it is also conceivable that +δ and −δ are replaced by +δ1 and −δ2 and each of δ1 and δ2 satisfies any of the (b1) expression to the (b3) expression. It should be noted that the setting value δ1 and δ2 representing the angle may be δ1=δ2 or δ1 ≠δ2.

Also, according to the above-mentioned embodiment, the example is illustrated in which the image pickup for the end part of the projection image of the wafer 1 and the calculation for the index values are performed for the three supporting positions including the reference supporting position and the respective supporting positions where the wafer 1 is rotated by +δ degrees and −δ degrees with respect to the position, but it is also conceivable that the image pickup for the end part of the projection image of the wafer 1 and the calculation for the index values are performed for the two supporting positions rotated with respect to the reference supporting position by +δ degrees and −δ degrees or four or more supporting positions including the two supporting positions.

For example, in the range from the supporting position where the wafer 1 is rotated by +δ degrees with respect to the reference supporting position to the supporting position rotated by −δ degrees, it is conceivable that the image pickup for the end part of the projection image of the wafer 1 and the calculation for the index values are performed for each of the respective supporting positions at ±δ degrees and supporting positions at the respective angles where the angle range is divided at equal angles into plural sections.

Also, it is conceivable that the control apparatus 10 or a computer (not shown) communicable with the control apparatus 10 is provided with the setting function of δ while executing a predetermined program.

For example, the control apparatus 10 is provided with a communication unit (an example of the measurement target width information input means) communicating with an operation input unit or an external apparatus such as a key board for inputting information such as a width occupied in the radius direction of the wafer 1 by a range for the target of the shape measurement in the end surface of the wafer 1 (hereinafter, referred to as measurement target width) and the radius r of the wafer 1, and furthermore, the processor provided with the control apparatus 10 performs a processing of calculating (setting) δ on the basis of the input measurement target width and the information on the radius and storing the calculated δ in the storage unit (an example of the setting angle calculation means).

Herein, the measurement target width is the chamfer width k in general, and in that case, the control apparatus 10 applies the chamfer width k and the radius r input, for example, to the expression $\delta = \cos^{-1}((r-k)/r)$ (equivalent to the (b3) expression) to calculate δ.

According to this, it is possible to easily set S suitable to the shape of the wafer 1 which is the measurement target.

Industrial Applicability

The present invention can be utilized to the shape measurement for the end surface of the disk-shaped measurement target such as mainly the semiconductor wafer and, in addition, the aluminum substrate and the glass substrate for the hard disk.

The invention claimed is:

1. A shape measurement apparatus comprising:
   a light transmission element configured to transmit light to a chamfer processed end part of a disk-shaped measurement target from a direction substantially parallel to respective front and rear surfaces of the measurement target;
   an image pickup device configured to pick up a projection image of an end surface of the measurement target from a direction opposite to the light transmitting direction;
   a rotation supporting mechanism configured to rotatably support the measurement target in a circumferential direction thereof;
   a rotation control device configured to support the measurement target by the rotation supporting mechanism in a range from a first supporting position rotated by a predetermined first set angle with respect to a predetermined reference supporting position to a second supporting position rotated by a predetermined second set angle having an opposite positive or negative sign with respect to the first set angle at two or more supporting positions including the first supporting position and the second supporting position;
   an image pickup control device configured to pick up by the image pickup means the projection image of the end surface of the measurement target supported by the rotation control means at the two or more supporting positions;
   an index value calculation device configured to calculate an index value of an end surface shape by executing a previously set image processing for each of a plurality of projection images obtained through a processing by the image pickup control device; and
   a measurement value derivation device configured to derivate a measurement value for the shape of the end surface of the measurement target corresponding to the reference supporting position by selecting one representative value based on the plurality of index values calculated by the index value calculation device or calculating one aggregate value while following a previously set rule, wherein in a case where the first set angle is denoted by +δ1 and the second set angle is denoted by −δ2, the δ1 and the δ2 satisfy the following expression:

$$\delta 1 \geq \cos^{-1}((r-k)/r)$$

$$\delta 2 \geq \cos^{-1}((r-k)/r)$$

r: Radius of the measurement target
   k: Chamfer width of the end surface of the measurement target.

2. The shape measurement apparatus according to claim 1, wherein:
   the rotation control device supports the measurement target by the rotation supporting mechanism at three or more supporting positions including the reference supporting position, the first supporting position, and the second supporting position; and
   the image pickup control device picks up by the image pickup means the projection image of the end surface of the measurement target supported at each of the three or more supporting positions by the rotation control device.

3. The shape measurement apparatus according to claim 1, wherein the previously set rule is any of a rule of selecting a median value, a smallest value, or a largest value among the plurality of the index values and a rule of calculating an average value for a previously set numbers of values in an order from a smaller one or a larger one among the plurality of index values.

4. A shape measurement apparatus comprising:
   a light transmission element configured to transmit light to a chamfer processed end part of a disk-shaped measurement target from a direction substantially parallel to respective front and rear surfaces of the measurement target;
   an image pickup device configured to pick up a projection image of an end surface of the measurement target from a direction opposite to the light transmitting direction;
   a rotation supporting mechanism configured to rotatably support the measurement target in a circumferential direction thereof;
   a rotation control device configured to support the measurement target by the rotation supporting mechanism in a range from a first supporting position rotated by a predetermined first set angle with respect to a predetermined reference supporting position to a second supporting position rotated by a predetermined second set angle having an opposite positive or negative sign with respect to the first set angle at two or more supporting positions including the first supporting position and the second supporting position;
   an image pickup control device configured to pick up by the image pickup device the projection image of the end surface of the measurement target supported by the rotation control device at the two or more supporting positions;
   index value calculation device configured to calculate an index value of an end surface shape by executing a previously set image processing for each of a plurality of projection images obtained through a processing by the image pickup control device; and measurement value derivation device configured to derivate a measurement value for the shape of the end surface of the measurement target corresponding to the reference supporting position by selecting one representative value based on the plurality of index values calculated by the index value calculation means or calculating one aggregate value while following a previously set rule, wherein the measurement target is a semiconductor wafer, and wherein in a case where the first set angle is denoted by +δ1 and the second set angle is denoted by −δ2, the δ1 and the δ2 satisfy the following expression:

$$22.5 \geq \delta 1 \geq \cos^{-1}((r-k)/r)$$

$$22.5 \geq \delta 2 \geq \cos^{-1}((r-k)/r)$$

r: Radius of the semiconductor wafer
k: Chamfer width of the end surface of the semiconductor wafer where, k/r <0.076.

5. The shape measurement apparatus according to claim 4, wherein in a case where the first set angle is denoted by +δ1 and the second set angle is denoted by −δ2, the δ1 and the δ2 are respectively in a range between 2° or larger and 22.5° or smaller.

6. The shape measurement apparatus according to claim 1, wherein the index value is any one of the chamfer width of the measurement target, a chamfer angle, and a chamfer radius.

7. A shape measurement method comprising:
transmitting light by a light transmission element to a chamfer processed end part of a disk-shaped measurement target from a direction substantially parallel to respective front and rear surfaces of the measurement target;
picking up a projection image of an end surface of the measurement target by an image pickup device from a direction opposite to the light transmitting direction;
supporting the measurement target by a rotation supporting mechanism rotatably supporting the measurement target in a circumferential direction thereof in a range from a first supporting position rotated by a predetermined first set angle with respect to a predetermined reference supporting position to a second supporting position rotated by a predetermined second set angle having an opposite positive or negative sign with respect to the first set angle at two or more supporting positions including the first supporting position and the second supporting position;
picking up by the image pickup device a plurality of projection images of the end surface of the measurement target supported at the respective supporting positions;
recording image pickup data in a predetermined storage device;
calculating a plurality of index values of an end surface shape by executing a previously set image processing by a predetermined computation device for each of the plurality of projection images; and
executing a processing of deriving a measurement value for the shape of the end surface of the measurement target corresponding to the reference supporting position by a predetermined computation device by selecting one representative value based on the plurality of index values calculated by the index value calculation device or calculating one aggregate value while following a previously set rule, wherein in a case where the first set angle is denoted by +δ1 and the second set angle is denoted by −δ2, the δ1 and the δ2 satisfy the following expression:

$$\delta 1 \geq \cos^{-1}((r-k)/r)$$

$$\delta 2 \geq \cos^{-1}((r-k)/r)$$

r: Radius of the measurement target
k: Chamfer width of the end surface of the measurement target.

8. The shape measurement method according to claim 7, wherein the measurement target is supported by the rotation supporting mechanism at three or more supporting positions including the reference supporting position, the first supporting position, and the second supporting position, and the projection image of the end surface of the measurement target supported at each of the three or more supporting positions is picked up by the image pickup device.

9. The shape measurement method according to claim 7, wherein the previously set rule is any of a rule of selecting a median value, a smallest value, or a largest value among the plurality of the index values and a rule of calculating an average value for a previously set numbers of values in an order from a smaller one or a larger one among the plurality of index values.

10. A shape measurement method comprising:
transmitting light by a light transmission element to a chamfer processed end part of a disk-shaped measurement target from a direction substantially parallel to respective front and rear surfaces of the measurement target;
picking up a projection image of an end surface of the measurement target by image pickup device from a direction opposite to the light transmitting direction;
supporting the measurement target by a rotation supporting mechanism rotatably supporting the measurement target in a circumferential direction thereof in a range from a first supporting position rotated by a predetermined first set angle with respect to a predetermined reference supporting position to a second supporting position rotated by a predetermined second set angle having an opposite positive or negative sign with respect to the first set angle at two or more supporting positions including the first supporting position and the second supporting position;
picking up by the image pickup device a plurality of projection images of the end surface of the measurement target supported at the respective supporting positions;
recording image pickup data in predetermined storage device;
calculating a plurality of index values of an end surface shape by executing a previously set image processing by predetermined computation device for each of the plurality of projection images; and
executing a processing of deriving a measurement value for the shape of the end surface of the measurement target corresponding to the reference supporting position by predetermined computation device by selecting one representative value based on the plurality of index values calculated by the index value calculation device or calculating one aggregate value while following a previously set rule, wherein the measurement target is a semiconductor wafer, and wherein in a case where the first set angle is denoted by +δ1 and the second set angle is denoted by −δ2, the δ1 and the δ2 satisfy the following expression:

$$22.5 \geq \delta 1 \cos^{-1}((r-k)/r)$$

$$22.5 \geq \delta 2 \cos^{-1}((r-k)/r)$$

r: Radius of the semiconductor wafer k: Chamfer width of the end surface of the semiconductor wafer where, k/r <0.076.

11. The shape measurement method according to claim 10, wherein in a case where the first set angle is denoted by +δ1 and the second set angle is denoted by −δ2, the δ1 and the δ2 are respectively in a range between 2° or larger and 22.5° or smaller.

12. The shape measurement method according to claim 7, wherein the index value is any one of the chamfer width of the measurement target, a chamfer angle, and a chamfer radius.

13. The shape measurement apparatus according to claim 1, wherein the measurement target is a semiconductor wafer.

14. The shape measurement apparatus according to claim 4, wherein:
- the rotation control device supports the measurement target by the rotation supporting mechanism at three or more supporting positions including the reference supporting position, the first supporting position, and the second supporting position; and
- the image pickup control device picks up by the image pickup device the projection image of the end surface of the measurement target supported at each of the three or more supporting positions by the rotation control device.

15. The shape measurement apparatus according to claim 4, wherein the previously set rule is any of a rule of selecting a median value, a smallest value, or a largest value among the plurality of the index values and a rule of calculating an average value for a previously set numbers of values in an order from a smaller one or a larger one among the plurality of index values.

16. The shape measurement apparatus according to claim 4, wherein the index value is any one of the chamfer width of the measurement target, a chamfer angle, and a chamfer radius.

17. The shape measurement apparatus according to claim 7, wherein the measurement target is a semiconductor wafer.

18. The shape measurement method according to claim 10, wherein the measurement target is supported by the rotation supporting mechanism at three or more supporting positions including the reference supporting position, the first supporting position, and the second supporting position, and the projection image of the end surface of the measurement target supported at each of the three or more supporting positions is picked up by the image pickup device.

19. The shape measurement method according to claim 10, wherein the previously set rule is any of a rule of selecting a median value, a smallest value, or a largest value among the plurality of the index values and a rule of calculating an average value for a previously set numbers of values in an order from a smaller one or a larger one among the plurality of index values.

20. The shape measurement method according to claim 10, wherein the index value is any one of the chamfer width of the measurement target, a chamfer angle, and a chamfer radius.

* * * * *